United States Patent
Brown

(10) Patent No.: US 11,861,765 B2
(45) Date of Patent: Jan. 2, 2024

(54) IMAGING SYSTEM DETECTOR CLIPPING-INDUCED BIAS CORRECTION

(71) Applicant: KONINKLIJKE PHILIPS N.V., Eindhoven (NL)

(72) Inventor: Kevin Martin Brown, Chardon, OH (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 535 days.

(21) Appl. No.: 17/258,182

(22) PCT Filed: Jul. 9, 2019

(86) PCT No.: PCT/EP2019/068315
§ 371 (c)(1),
(2) Date: Jan. 6, 2021

(87) PCT Pub. No.: WO2020/011739
PCT Pub. Date: Jan. 16, 2020

(65) Prior Publication Data
US 2021/0272333 A1     Sep. 2, 2021

Related U.S. Application Data

(60) Provisional application No. 62/695,249, filed on Jul. 9, 2018.

(51) Int. Cl.
G06T 11/00     (2006.01)
A61B 6/03      (2006.01)
A61B 6/00      (2006.01)

(52) U.S. Cl.
CPC ............ G06T 11/005 (2013.01); A61B 6/032 (2013.01); A61B 6/4233 (2013.01);
(Continued)

(58) Field of Classification Search
CPC ... G06T 11/005; G06T 2211/40; A61B 6/032; A61B 6/4233; A61B 6/5205; A61B 6/5258; A61B 6/582
See application file for complete search history.

(56) References Cited

U.S. PATENT DOCUMENTS 5,533,091 A      7/1996  Hsieh
6,628,744 B1 *   9/2003  Luhta ................... G06T 11/005
                                                    378/15
(Continued)

FOREIGN PATENT DOCUMENTS

DE   102011078459 A1   1/2013
JP      2005253628 A   9/2005
(Continued)

OTHER PUBLICATIONS

Kevin M. Brown, "Clipping-induced bias correction for low-dose CT imaging," Proc. SPIE 11072, 15th International Meeting on Fully Three-Dimensional Image Reconstruction in Radiology and Nuclear Medicine, 110721O (May 28, 2019); doi: 10.1117/12.2531708 (Year: 2019).*

(Continued)

*Primary Examiner* — Andrae S Allison
(74) *Attorney, Agent, or Firm* — Larry Liberchuk

(57) ABSTRACT

A system (116) includes an unlogger (202) configured to unlog logged data, to produce unlogged clipped data. The logged data includes attenuation line integrals and clipping-induced bias. The system further includes a mean estimator (204) configured to estimate a mean value of the unlogged clipped data. The system further includes a correction determiner (206) configured to determine correction to the clipping-induced bias based on the estimated mean value of the unlogged clipped data. The system further includes an adder (Continued)

(210) configured to correct the logged data with the correction to produce corrected logged data.

18 Claims, 6 Drawing Sheets

(52) U.S. Cl.
CPC .......... *A61B 6/5205* (2013.01); *A61B 6/5258* (2013.01); *A61B 6/582* (2013.01); *G06T 2211/40* (2013.01)

(56) References Cited

U.S. PATENT DOCUMENTS

| | | | |
|---|---|---|---|
| 6,671,345 B2 | 12/2003 | Vrettos | |
| 9,031,299 B2 | 5/2015 | Brown | |
| 2003/0076988 A1 | 4/2003 | Liang | |
| 2005/0201635 A1* | 9/2005 | Mori | G06T 11/005 378/4 |
| 2007/0058771 A1* | 3/2007 | Sauer | G06T 11/005 378/4 |
| 2013/0208971 A1* | 8/2013 | Brown | G06T 11/005 382/131 |
| 2013/0243349 A1 | 9/2013 | Yang | |
| 2017/0135659 A1 | 5/2017 | Wang | |
| 2017/0249723 A1* | 8/2017 | Karbeyaz | G06T 5/002 |
| 2018/0096476 A1* | 4/2018 | Tang | G06T 11/005 |
| 2019/0231224 A1* | 8/2019 | Rupcich | A61B 6/032 |
| 2019/0295249 A1* | 9/2019 | Schaefer | G16H 30/40 |
| 2021/0389399 A1* | 12/2021 | Wang | A61B 6/4258 |
| 2022/0061793 A1* | 3/2022 | Vaz | A61B 6/54 |

FOREIGN PATENT DOCUMENTS

| | | |
|---|---|---|
| WO | WO2017223560 A1 | 12/2017 |
| WO | WO2020011739 A1 | 1/2020 |

OTHER PUBLICATIONS

Tilley S 2nd, Siewerdsen JH, Stayman JW. Iterative CT Reconstruction using Models of Source and Detector Blur and Correlated Noise. Conf Proc Int Conf Image Form Xray Comput Tomogr. 2014;2014:363-367. PMID: 25346949; PMCID: PMC4207223. (Year: 2014).*

PCT International Search Report, International application No. PCT/EP2019/068315, dated Sep. 5, 2019.

Chang Zhiqian et al., "Modeling and Pre-Treatment of Photon-Starved CT Data for Iterative Reconstruction", IEEE Transactions on Medical Imaging, IEEE Service Center, Piscataway, NO, US, vol. 36, No. 1, Jan. 1, 2017 (Jan. 1, 2017), pp. 277-287, XP011638323.

* cited by examiner

IMAGING SYSTEM DETECTOR CLIPPING-INDUCED BIAS CORRECTION

FIELD OF THE INVENTION

The following generally relates to imaging and more particularly to imaging system detector clipping-induced bias correction, and is described with particular application to computed tomography (CT).

BACKGROUND OF THE INVENTION

A CT scanner has included a detector array with a plurality of detector pixels that each produce intensity measurements indicative of x-ray attenuation along paths of x-ray photons through an object, and detector electronics that process the measurements with at least an analog-to-digital (A/D) converter that is configured to perform a logarithmic operation that converts the digitized measurements into attenuation line integrals. The attenuation line integrals are pre-processed via a calibration(s) and/or a correction(s) and then reconstructed to generate volumetric image data.

In low-dose CT imaging applications, e.g., such as lung cancer screening with a dose level of 30-50 milliampere-second (mAs), the number of x-ray photons impinging the detector pixels during scanning, for at least some data acquisition intervals, can become so low that the detector output signal is or mainly is electronic noise of the detector electronics. In this instance, after bias signal subtraction, some of the measurements become negative. Since the logarithmic operation is undefined for values less than or equal to zero, the negative values are "clipped" to small positive values.

This clipping shifts the mean value of the measurements. Unfortunately, this shift in the mean value introduces a dark shading artifact (referred to herein as "clipping-induced bias" artifact) in the reconstructed volumetric image data. This artifact degrades image quality. As such, a diagnostic quality of the volumetric image data may be compromised, relative to volumetric image data without the clipping-induced bias artifact. Hence, there is an unresolved need for an approach to mitigate this clipping-induced bias artifact in the volumetric image data.

SUMMARY OF THE INVENTION

Aspects described herein address the above-referenced problems and others.

In one aspect, a system includes an unlogger configured to unlog logged data to produce unlogged clipped data. The logged data includes attenuation line integrals and clipping-induced bias. The system further includes a mean estimator configured to estimate a mean value of the unlogged clipped data. The system further includes a correction determiner configured to determine a correction to the clipping-induced bias based on the estimated mean value of the unlogged clipped data. The system further includes an adder configured to correct the logged data with the correction to produce corrected logged data.

In another aspect, a computer readable medium is encoded with computer executable instructions, which, when executed by a processor of a computer, cause the processor to: unlog logged data, which includes attenuation line integrals and clipping-induced bias, to produce unlogged clipped data, estimate a mean value of the unlogged clipped data, determine a correction to the clipping-induced bias based on the estimated mean value of the unlogged clipped data, and correct the logged data with the correction to produce corrected logged data.

In another aspect, a method includes unlogging logged data, which includes attenuation line integrals and clipping-induced bias, to produce unlogged clipped data. The method further includes estimating a mean value of the unlogged clipped data. The method further includes determining a correction to the clipping-induced bias based on the estimated mean value of the unlogged clipped data. The method further includes correcting the logged data with the correction to produce corrected logged data.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF EMBODIMENTS

The following describes an example imaging system with a clipping-induced bias corrector configured to correct for clipping-induced bias introduced into the data by a mathematical logging operation of the data. The clipping-induced bias correction mitigates clipping-induced bias artifact in the reconstructed volumetric image data.

Figure 1:
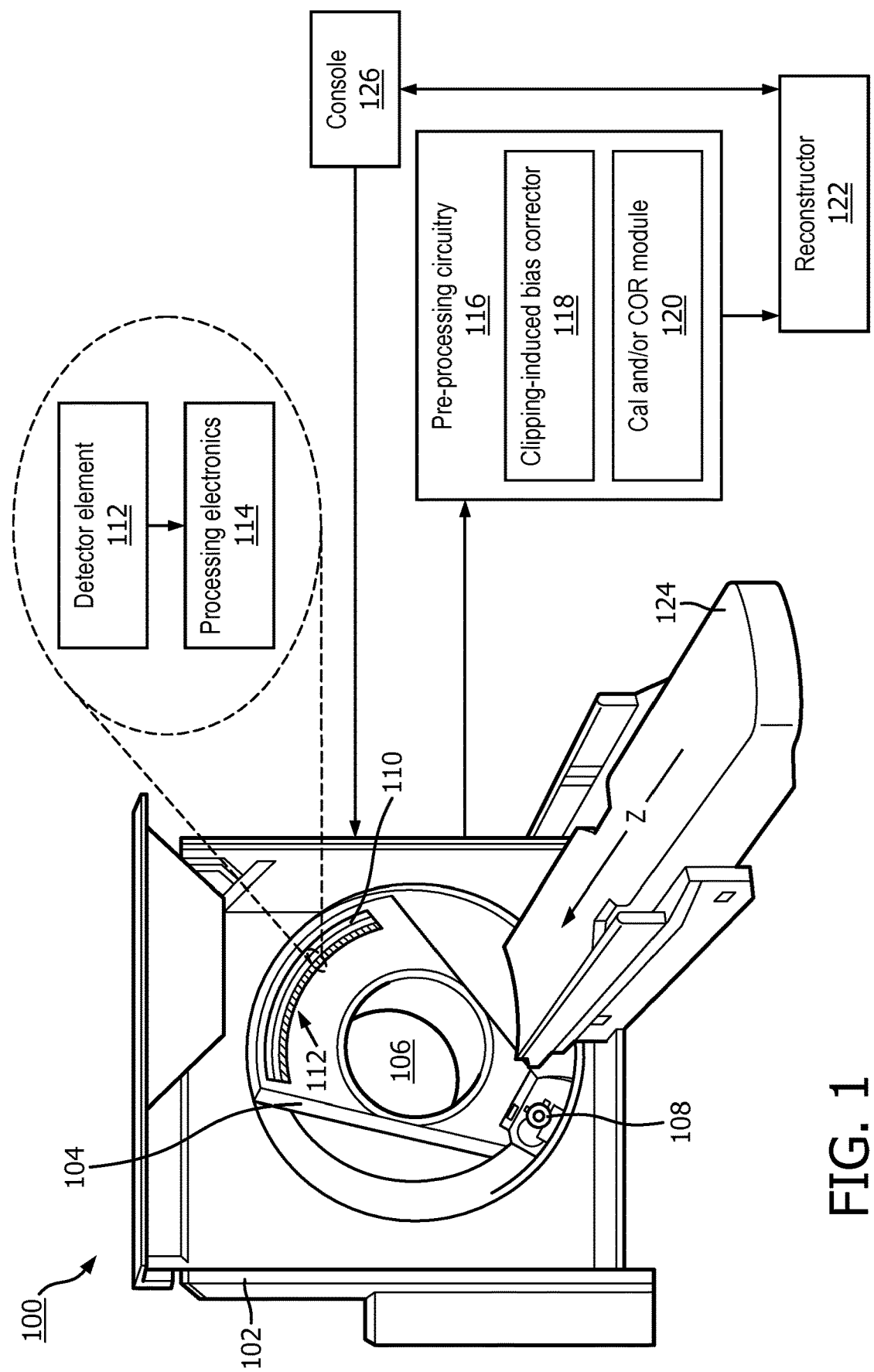
FIG. 1 schematically illustrates an example imaging system with pre-processing circuitry that includes at least a clipping-induced bias corrector.

FIG. 1 schematically illustrates an imaging system 100, such as a computed tomography (CT) scanner. Suitable CT scanners include scanners configured for non-spectral and/or spectral imaging.

The imaging system 100 includes a generally stationary gantry 102 and a rotating gantry 104, which is rotatably supported by the stationary gantry 102 and rotates around an examination region 106 about a z-axis. The imaging system 100 further includes a radiation source 108, such as an x-ray tube. The radiation source 108 is rotatably supported by the rotating gantry 104, rotates with the rotating gantry 104, and emits x-ray radiation that traverses the examination region 106.

The imaging system 100 further includes a one- or two-dimensional detector array 110 of rows of detector elements 112. The detector array 110 is rotatably supported by the rotating gantry 104 along an angular arc opposite the radiation source 108 across the examination region 106. The detector array 110 rotates in coordination with the radiation source 108, detects x-ray radiation (i.e. x-ray photons) that traverses the examination region 106, and generates intensity measurement electrical signals indicative of the detected x-ray radiation. A set of measurements for each acquisition interval is referred to herein as a view.

The imaging system 100 further includes processing electronics 114 configured to process the electrical signals. In this example, the processing electronics 114 include an analog-to-digital (A/D) converter that digitizes the electrical signals. In one instance, the A/D converter is implemented as a current-to-frequency (I/F) converter that generates a train of pulses with a frequency proportional to an input electrical current signal. An example of such a converter is described in U.S. Pat. No. 6,671,345 B2, filed Nov. 7, 2001, and entitled "Data Acquisition for Computed Tomography," which is incorporated herein by reference in its entirety. The A/D converter also takes a log of the digitized signals, producing attenuation line integrals (logged data). As discussed herein, the logging operation clips negative values, which shifts the mean (clipping-induced bias) of the measurements.

The imaging system 100 further includes pre-processing circuitry 116. The illustrated pre-processing circuitry 116 includes at least a clipping-induced bias corrector 118 and a calibration and/or correction (cal and/or cor) module 120. As described in greater detail below, the clipping-induced bias corrector 118 is configured to correct for the clipping-induced bias introduced by the logging operation, producing corrected logged data. The calibration and/or correction module 120 is configured to perform calibrations and/or corrections for physical and/or component effects before and/or after the clipping-induced bias correction. Examples include air scan calibration, off-focal radiation correction, beam hardening correction, scatter correction, de-noising, and/or other known CT calibrations and/or corrections.

The imaging system 100 further includes a reconstructor 122 configured to reconstruct the pre-processed logged data and generate volumetric image data. A subject support 124, such as a couch, supports an object or subject in the examination region 106. The subject support 124 is movable in coordination with performing an imaging procedure so as to guide the subject or object with respect to the examination region 106 for loading, scanning, and/or unloading the subject or object. An operator console 126 allows an operator to control an operation of the system 100 such as selecting a scanning protocol, a reconstruction algorithm, etc. The operator console 126 includes an input device(s) such as a mouse, keyboard, etc. and an output device(s) such as a display monitor.

Figure 2:
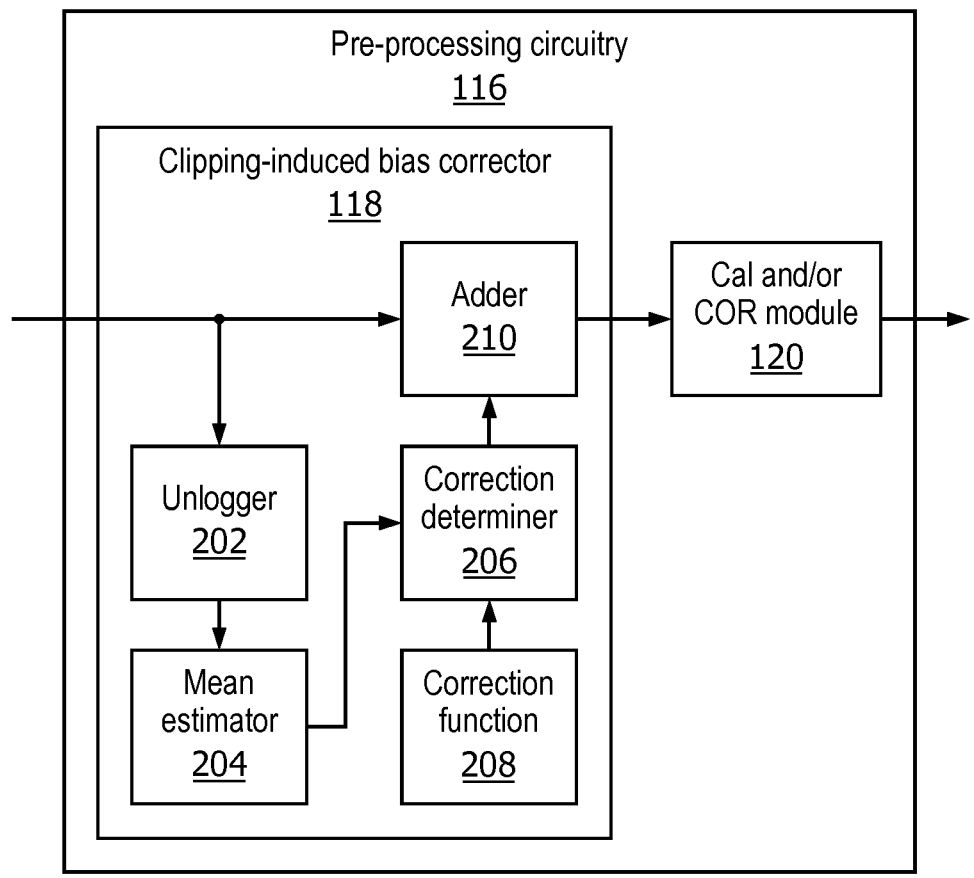
FIG. 2 schematically illustrates an example of the pre-processing circuitry of FIG. 1.

FIG. 2 schematically illustrates an example of the pre-processing circuitry 116.

The illustrated clipping-induced bias corrector 118 includes an unlogger 202. The unlogger 202 is configured to unlog the logged data from the processing electronics 114, producing clipped data. As discussed herein, the logging operation clips negative values, which are permanently lost, and the unlogging operation does not restore the lost (clipped) negative values.

The illustrated clipping-induced bias corrector 118 further includes a mean estimator 204. The mean estimator 204 is configured to estimate a mean value of the clipped data. In one instance, this is achieved by applying a filter (e.g., a 3-D smoothing filter) to the clipped data and determining a mean value of the smoothed data. In another instance, a deep learning algorithm is employed to estimate the mean value of the clipped data. Other approaches are also contemplated herein.

Figure 3:
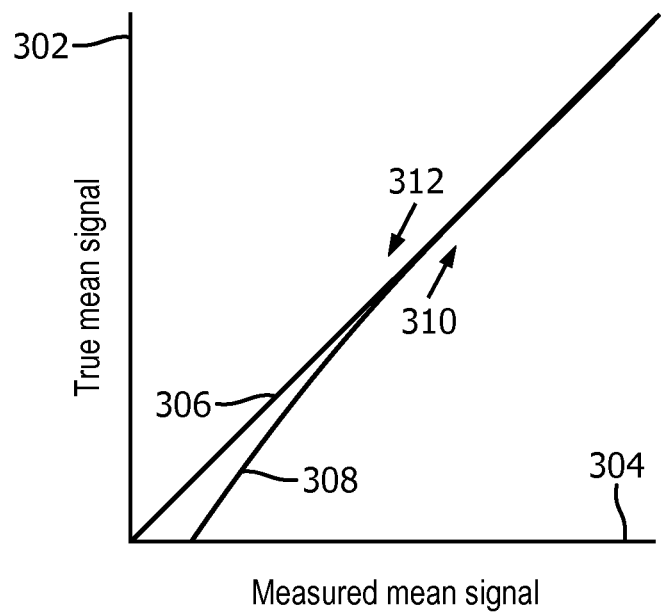
FIG. 3 illustrates an example correction function employed by the pre-processing circuitry of FIG. 1 to remove clipping-induced bias artifact.

The illustrated clipping-induced bias corrector 118 further includes a correction determiner 206. The correction determiner 206 is configured to determine a correction for the clipping-induced bias based on the mean value of the clipped data and a predetermined correction function 208. FIG. 3 illustrates an example of the correction function 208. In FIG. 3, a first (y-) axis 302 represents a mean of the unclipped data (i.e. the true mean) and a second (x-) axis 304 represents a mean of the measured data.

A first plot 306 shows a relationship between the true mean of the unclipped data and a theoretical measurement of the mean of the unclipped data. The measurement is theoretical because the negative values lost during the logging operation are not recoverable. The first plot 306 shows a one-to-one relationship between the true mean and the theoretical measured mean. As shown, without the clipping, the theoretical measured mean is or is close to the true mean of the original data.

A second plot 308 is a plot of the estimate of the mean value of the clipped data. From the second plot 308, the relationship between the true mean of the unclipped data and the estimated mean of the clipped data is approximately one-to-one for higher mean values 310. However, for lower mean values 312, the estimate of the mean value of the clipped data falls off non-linearly. The second plot 308 is generated analytically, through Monte-Carlo simulations with Poisson and Gaussian random variables, or through calibration scans with known objects and tube currents, and/or otherwise.

Returning to FIG. 2, and with further reference to FIG. 3, the correction determiner 206 determines a shift in the mean (i.e. the clipping-induced bias) as a difference between corresponding points of the first and second plots 306 and 308. The correction determiner 206 generates a low-frequency correction based on the shift. In one instance, the correction is $$-\log\left(1 - \frac{\text{bias}}{p_m}\right),$$

where bias=$P_m - P_T$, $P_m$(d, r, v) represents the measured mean of the clipped data, $P_T$(d, r, v) represents the true mean, and p(d, r, v) represents the clipped data, for each detector element d, row r, and view v.

The illustrated clipping-induced bias corrector 118 further includes an adder 210. The adder 210 adds the logged data (−log(p)) and the correction $$\left(-\log\left(1 - \frac{\text{bias}}{p_m}\right)\right)$$

to produce corrected logged data $$\left(\log_{corr} = -\log(x) - \log\left(1 - \frac{\text{bias}}{p_m}\right)\right).$$

Note that the correction cannot simply be the bias at least because subtracting the bias from each point in the unlogged data would introduce additional bias for noisy signals close to zero because of the non-linearity of the logarithm operation.

The calibration and/or correction module 120 performs calibrations and/or corrections to the corrected logged data, and the reconstructor 122 reconstructs the calibrated and/or corrected data.

Figure 4:
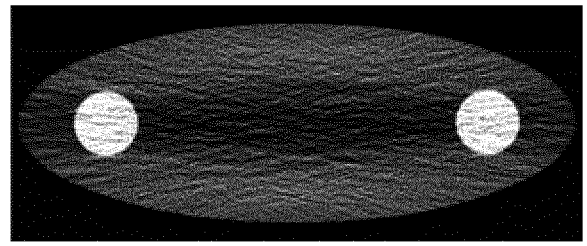
FIG. 4 illustrates an image generated without the approach described herein and including clipping-induced bias artifact.
Figure 5:
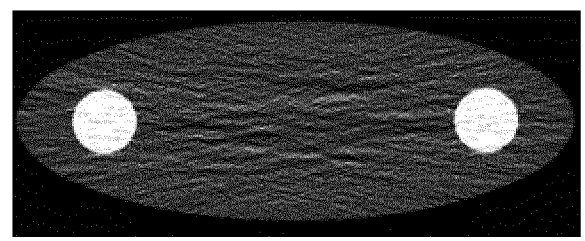
FIG. 5 illustrates an image generated with the approach described herein to remove clipping-induced bias artifact.

FIG. 4 shows an example of an image with clipping-induced bias artifact, which manifests as dark shading, which is more predominant along longer paths since more photons are attenuated and less photons will reach the detector array 110. FIG. 5 shows an example of an image reconstructed from the same measurements as the image in FIG. 4, but with the clipping-induced bias removed via the correction described herein. Relative to FIG. 4, the dark shading is removed and/or reduced in the image of FIG. 5.

Figure 6:
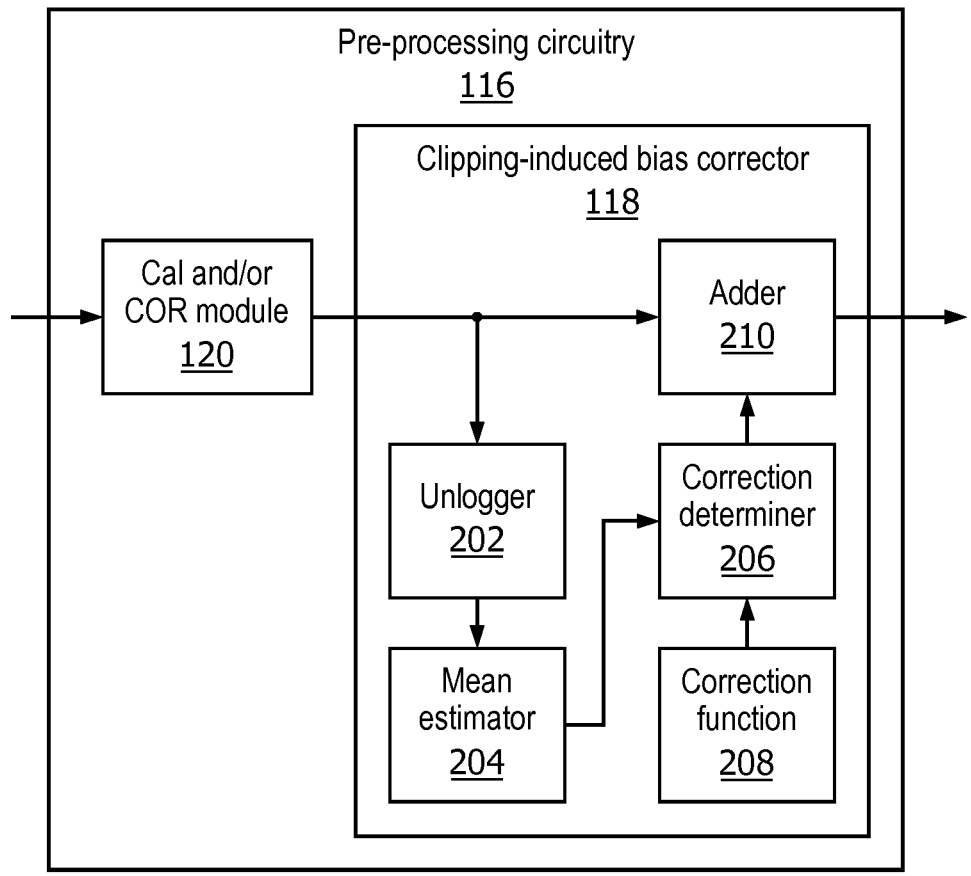
FIG. 6 schematically illustrates another example of the pre-processing circuitry of FIG. 1.

FIG. 6 schematically illustrates a variation of the pre-processing circuitry 116 described in connection with FIG. 2. In this variation, the calibration and/or correction module 120 performs calibrations and/or corrections to the uncorrected logged data, which is then corrected for clipping-induced bias, as described herein, and reconstructed to generate volumetric image data.

Figure 7:
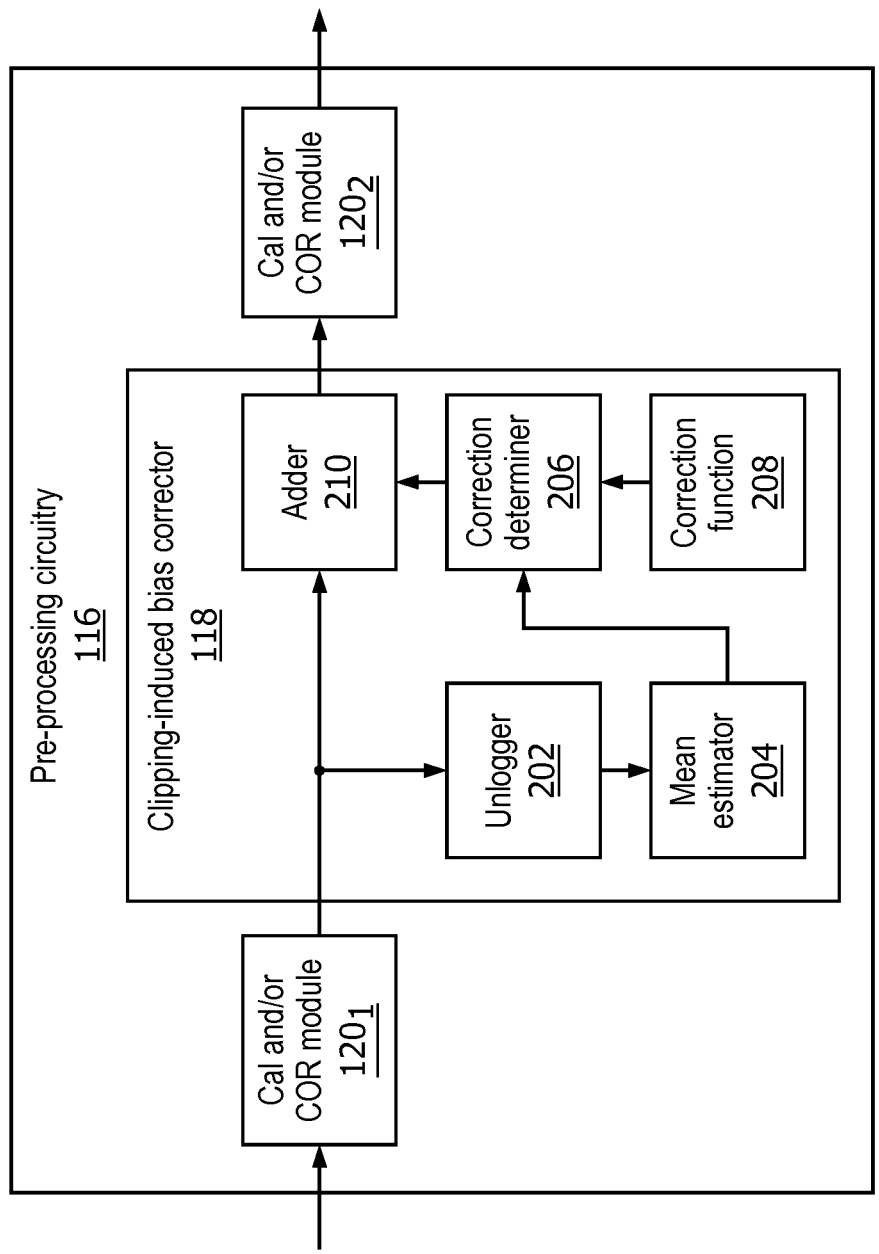
FIG. 7 schematically illustrates another example of the pre-processing circuitry of FIG. 1.

FIG. 7 schematically illustrates another variation of the pre-processing circuitry 116 described in connection with FIG. 2. In this variation, a first set of calibrations and/or corrections $120_1$ is performed to the uncorrected logged data, and a second set of calibrations and/or corrections $120_2$ is performed to the corrected logged data. Generally, this variation represents a combination of FIGS. 2 and 6.

Figure 8:
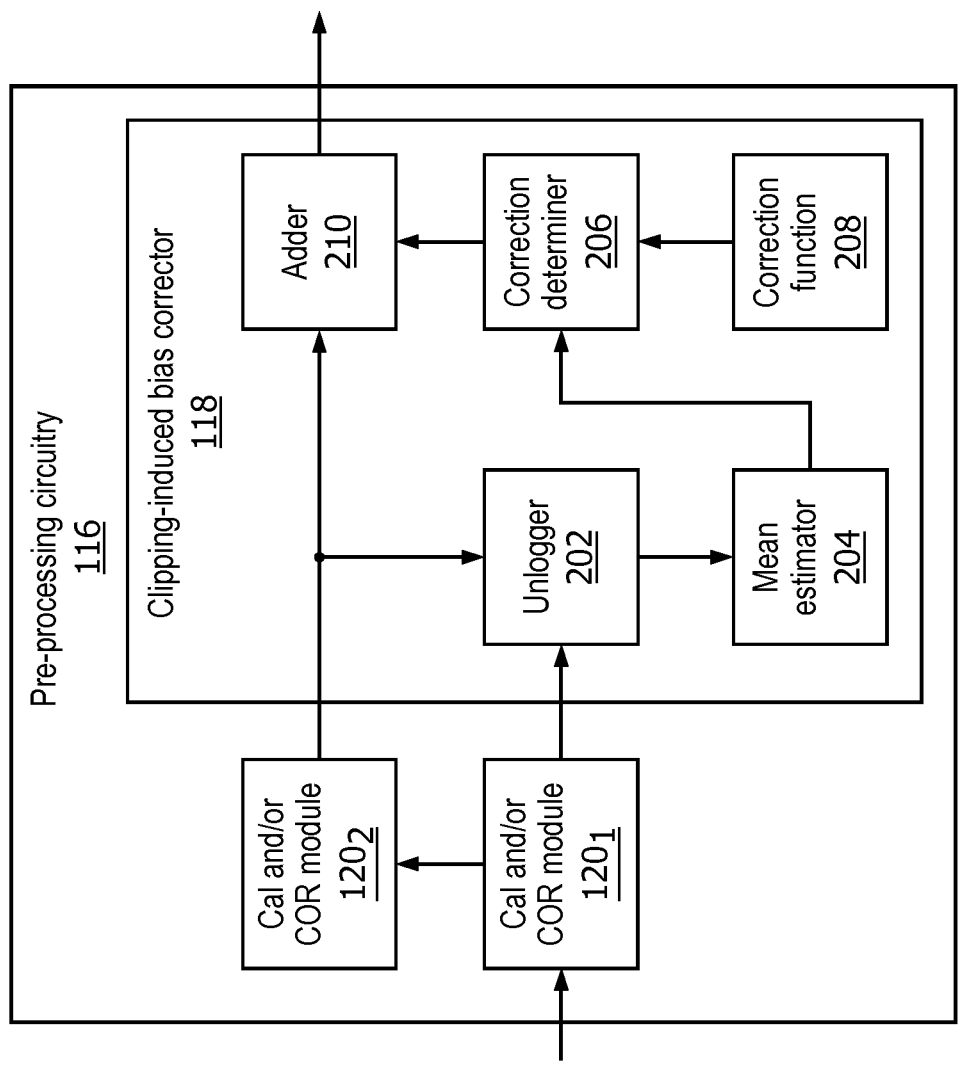
FIG. 8 schematically illustrates another example of the pre-processing circuitry of FIG. 1.

FIG. 8 schematically illustrates another variation of the pre-processing circuitry 116 described in connection with FIG. 2. In this variation, a first set of calibrations and/or corrections $120_1$ is performed to the uncorrected logged data and the partially calibrated and/or corrected data is conveyed to the unlogger 202, which processes the partially calibrated and/or corrected data as described herein.

A second set of calibrations and/or corrections $120_2$ is performed to the partially calibrated and/or corrected data and conveyed to the adder 210. In one instance, the first set $120_1$ does not include denoising, and the second set $120_2$ includes denoising. An example of suitable denoising is described in U.S. Pat. No. 9,031,299 B2, filed Apr. 17, 2013, and entitled "Low Dose CT Denoising," which is incorporated herein by reference in its entirety.

Figure 9:
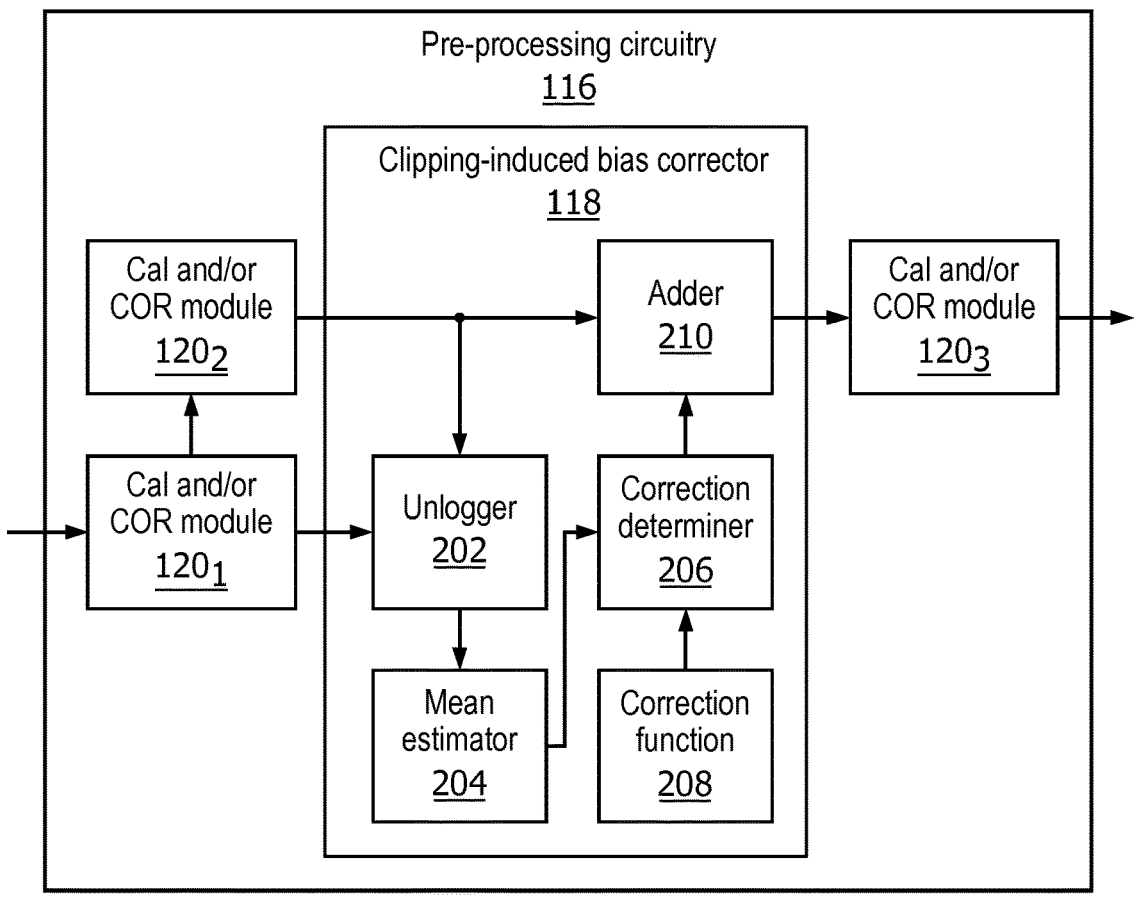
FIG. 9 schematically illustrates another example of the pre-processing circuitry of FIG. 1.

FIG. 9 schematically illustrates another variation of the pre-processing circuitry 116 described in connection with FIG. 2. In this variation, the first set of calibrations and/or corrections $120_1$ is performed to the uncorrected logged data and the partially calibrated and/or corrected data is conveyed to the unlogger 202, the second set of calibrations and/or corrections $120_2$ is performed to the partially calibrated and/or corrected data and conveyed to the logger adder 210, and a third second set of calibrations and/or corrections $120_3$ is performed to corrected logged data.

Figure 10:
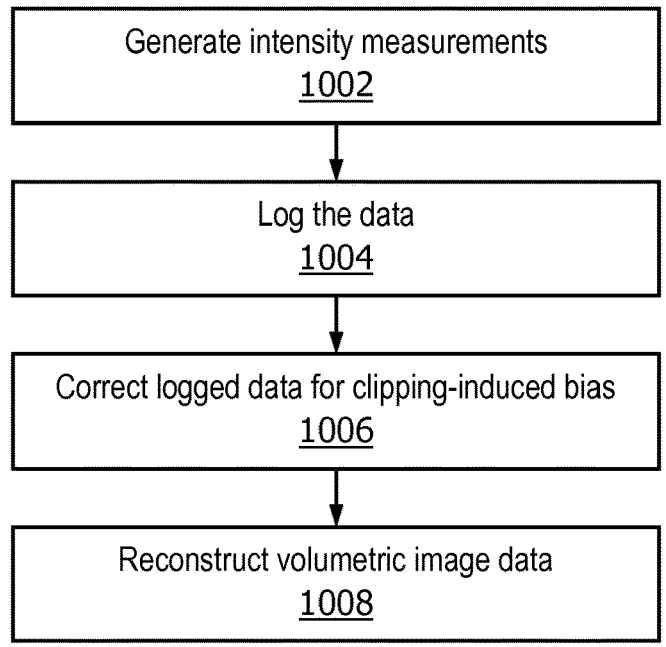
FIG. 10 illustrates an example method in accordance with an embodiment(s) described herein.

FIG. 10 illustrates an example method in accordance with an embodiment(s) described herein. It is to be appreciated that the ordering of the below acts is not limiting, and other ordering is contemplated herein, such as other serial processing and/or parallel processing.

At 1002, a scan is performed, producing intensity measurements.

At 1004, the intensity measurements are logged, creating logged data, which include a clipping-induced bias, which shifts a mean value of the measurements.

At 1006, the logged data is corrected for the clipping-induced bias, as described herein and/or otherwise. Calibrations and/or corrections for physical and/or component effects can be performed before and/or after the clipping-induced bias correction.

At 1008, the corrected logged clipped data is reconstructed to generate volumetric image data.

The above may be implemented by way of computer readable instructions, encoded or embedded on computer readable storage medium (which excludes transitory medium), which, when executed by a computer processor(s) (e.g., central processing unit (CPU), microprocessor, etc.), cause the processor(s) to carry out acts described herein. Additionally, or alternatively, at least one of the computer readable instructions is carried by a signal, carrier wave or other transitory medium, which is not computer readable storage medium.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A computed tomography (CT) imaging system, comprising:
   processing circuitry; and
   a memory containing instructions that, when executed by the processing circuitry, configure the imaging CT system to:
   unlog logged data, which includes attenuation line integrals and clipping-induced bias, to produce unlogged clipped data, wherein the logged data was acquired by a computed tomography scanner;
   estimate a mean value of the unlogged clipped data;
   determine a correction to the clipping-induced bias based on the estimated mean value of the unlogged clipped data; and
   correct the logged data with the correction to produce corrected logged data.

2. The CT imaging system of claim 1, wherein the correction is based on at correction function.

3. The CT imaging system of claim 2, wherein the correction function indicates a shift in a mean value between a true mean of unclipped data, which is logged to create the logged data, and the mean of the unlogged clipped data.

4. The CT imaging system of claim 1, wherein the one or more calibrations and/or one or more corrections is applied to the corrected logged data.

5. The CT imaging system of claim 1, wherein the one or more calibrations and/or one or more corrections is applied to the logged data.

6. The CT imaging system of claim 1, wherein one or more sets of calibrations and/or corrections is applied to the logged data, and a different set of calibrations and/or corrections is applied to the corrected logged data.

7. The CT imaging system of claim 1,
wherein the corrected logged data is reconstructed to produce volumetric image data.

8. The CT imaging system of claim 1, further comprising:
a detector array; and
processing electronics of the detector array configured to generate the logged data in response to detecting x-ray radiation.

9. A non-transitory computer readable medium encoded with computer executable instructions, where the computer executable instructions, when executed by at least one processor, cause the at least one processor to:
unlog logged data, which includes attenuation line integrals and clipping-induced bias, to produce unlogged clipped data;
estimate a mean value of the unlogged clipped data;
determine a correction to the clipping-induced bias based on the estimated mean value of the unlogged clipped data; and
correct the logged data with the correction to produce corrected logged data.

10. The non-transitory computer readable medium of claim 9, wherein the instructions further cause the processor to:
determine the correction based on a correction function.

11. The non-transitory computer readable medium of claim 10, wherein correction function indicates a shift in a mean value between a true mean of unclipped data and the mean of the unlogged clipped data.

12. The non-transitory computer readable medium of claim 9, wherein the instructions further cause the processor to:
apply one or more calibrations and/or one or more corrections before and/or after correcting the logged data.

13. The non-transitory computer readable medium of claim 9, wherein the instructions further cause the processor to:
reconstruct the corrected logged data to produce volumetric image data.

14. A CT imaging method, comprising:
unlogging logged data, which includes attenuation line integrals and clipping-induced bias, to produce unlogged clipped data;
estimating a mean value of the unlogged clipped data;
determining a correction to the clipping-induced bias based on the estimated mean value of the unlogged clipped data; and
correcting the logged data with the correction to produce corrected logged data.

15. The method of claim 14, further comprising:
determining the correction based on a correction function.

16. The method of claim 15, wherein correction function indicates a shift in a mean value between a true mean of unclipped data and the mean of the unlogged clipped data.

17. The method of claim 14, further comprising:
applying one or more calibrations and/or one or more corrections before and/or after correcting the logged data.

18. The method of claim 14, further comprising:
reconstructing the corrected logged data to produce volumetric image data.

\* \* \* \* \*